United States Patent [19]

Havlik et al.

[11] Patent Number: 5,780,452
[45] Date of Patent: Jul. 14, 1998

[54] ANTIMALARIAL DRUG

[75] Inventors: Ivan Havlik, Johannesburg, South Africa; Yutaro Kaneko; Tohru Mimura, both of Tokyo, Japan; Goro Chihara, Yokohama, Japan

[73] Assignee: Ajinomoto Co., Inc., Tokyo, Japan

[21] Appl. No.: 424,493

[22] PCT Filed: Sep. 20, 1994

[86] PCT No.: PCT/JP94/01544

§ 371 Date: Sep. 7, 1995

§ 102(e) Date: Sep. 7, 1995

[87] PCT Pub. No.: WO95/08334

PCT Pub. Date: Mar. 30, 1995

[30] Foreign Application Priority Data

Sep. 20, 1993 [JP] Japan .................................. 5-233296

[51] Int. Cl.$^6$ .......................... A61K 31/715; A61K 31/73; A61K 31/725
[52] U.S. Cl. ........................... 514/54; 514/55; 514/56; 514/58
[58] Field of Search ..................... 514/54, 55, 56, 514/58

[56] References Cited

U.S. PATENT DOCUMENTS 5,512,672  4/1996  Yamamoto et al. .................. 536/118

FOREIGN PATENT DOCUMENTS 62 215529  9/1987  Japan .
WO 92/05790  4/1992  WIPO .

OTHER PUBLICATIONS

Database WPI, Derwent Publications, AN–66–09413F [00], JP–B–63020141, 1988.

Transactions of the Royal Society of Tropical Medicine and Hygiene, vol. 88, No. 6, pp. 686–687, Nov. 1994, Ivan Havlik et al., "The Effect of Curdlan Sulphate On In Vitro Growth of Plasmodium Falciparum".

Biochemical Parmacology, vol. 39, No. 4 (1990), pp. 793–797.

*Primary Examiner*—Jerome D. Goldberg
*Attorney, Agent, or Firm*—Oblon, Spivak, McClelland, Maier & Neustadt, P.C.

[57] ABSTRACT

A novel antimalarial drug having high therapeutic effect, which comprises a sulfated polysaccharide or a pharmaceutically acceptable salt thereof as an active ingredient or both of a sulfated polysaccharide or a pharmaceutically acceptable salt thereof and quinine as active ingredients, is disclosed.

2 Claims, 3 Drawing Sheets

EFFECT OF CRDS TO INHIBIT THE INFECTION OF HUMAN ERYTHROCYTES

EFFECT OF JOINT USE OF CRDS AND QUININE
TO INHIBIT MALARIA PARASITE INFECTION

EFFECT OF CRDS AGAINST THE PARASITE GROWTH IN THE MOUSE BODY

ANTIMALARIAL DRUG

(TECHNICAL FIELD)

This invention relates to an antimalarial drug which comprises a sulfated polysaccharide as an active ingredient and another antimalarial drug which comprises quine in addition to a sulfated polysaccharide.

(BACKGROUND ART)

Malaria is a disease caused by plasmodia or malaria parasites, and quinine, chloroquine, primaquine and the like are currently used as typical therapeutic drugs, which, however, are not always sufficiently effective because of the generation of resistant parasites against these drugs. Also, it is known that sulfated polysaccharide are possessed of an anti-blood coagulation activity, an antiretroviral activity (Japanese Patent Application Laid-Open (Kokai) No. Sho 62-215529) and the like.

In such prior art background, it is an object of the present invention to provide a new antimalarial drug which has higher therapeutic effect.

(DISCLOSURE OF THE INVENTION)

With the aim of resolving the aforementioned problems, the inventors of the present invention have conducted intensive studies and found as the result that a sulfated polysaccharide has an antimalarial activity and that joint use of the sulfated polysaccharide and quinine exerts synergistic effect on the antimalarial activity. The present invention has been accomplished on the basis of these findings.

Accordingly, the present invention relates to an antimalarial drug which comprises a sulfated polysaccharide or a pharmaceutically acceptable salt thereof as an active ingredient and to another antimalarial drug similar to the above drug which further comprises quinine as another active ingredient.

Firstly, the former one, namely an antimalarial drug which comprises a sulfated polysaccharide or a pharmaceutically acceptable salt thereof as an active ingredient, will be described.

Examples of the sulfated polysaccharide to be used as an active ingredient of the antimalarial drug of the present invention include synthetic or natural sulfated polysaccharide such as sulfated curdlan, dextrin sulfate, chondroitin sulfate, heparin, carrageenan and the like. Of these, sulfated curdlan is preferred because it is weak in anticoagulation activity as a side effect. The sulfated polysaccharide having a sulfur content of from 5 to 25% by weight, preferably from 10 to 20% by weight, and most preferably from 12 to 17% by weight, and a weight average molecular weight of from 5,000 to 500,000, preferably from 20,000 to 200,000, and most preferably from 50,000 to 120,000, when measured by the gel filtration method (GPC), are preferably used.

Examples of the pharmaceutically acceptable salts of the sulfated polysaccharide include inorganic salts such as sodium salt, potassium salt, calcium salt, magnesium salt and the like.

The antimalarial drug of the present invention can be made into optional dosage forms such as injections, drippings, suppositories and the like with no particular limitation.

Preparation of the active ingredient of the present invention into a pharmaceutical drug can be made in the usual way, also with no particular limitation, making use of fillers or carriers such as lactose, glucose, mannitol, maltose, amino acids, gelatin, distilled water, ethanol and the like.

Dose of the antimalarial drug of the present invention varies depending on the age, body weight and symptoms of each patient and its administration method, and is generally from 1 to 1,000 mg/kg weight-day, preferably from 10 to 500 mg/kg weight-day, in terms of the active ingredient. The antimalarial drug of the present invention can be administered continuously or repeatedly.

The antimalarial drug of the present invention exerts its antimalarial effect when administered before or after malarial infection.

Next, the latter one, namely an antimalarial drug which comprises a sulfated polysaccharide or a pharmaceutically acceptable salt thereof and quinine as active ingredients, will be described.

As described in the foregoing, according to the findings of the present inventors, a sulfated polysaccharide and quinine exert synergistic effect in terms of antimalarial activity. That is, when the sulfated polysaccharide to be used according to the present invention is used jointly with quinine which is a conventional antimalarial drug, higher therapeutic effect is obtained in comparison with the arithmetic total of their therapeutic effects when used separately (see Test Example 2 which will be described later).

In this case, the sulfated polysaccharide and quinine may be administered in a ratio of from 20:1 to 20,000:1 (sulfated polysaccharide:quinine), and the dose may be 0.5 to 500 mg/kg weight-day, preferably 5 to 200 mg/kg body-day, in terms of a total of both active ingredients.

(BEST MODE FOR CARRYING OUT THE INVENTION)

The following examples are provided to illustratively describe the present invention, but the technical scope of the present invention is not limited thereby.

Test Example 1

Examination was made on the effect of sulfated curdlan sodium (CRDS; molecular weight, 80,000; sulfur content, 14.5%) on the infection of human erythrocytes with merozoites of a chloroquine-resistant malaria parasite *Plasmodium falciparum* strain FCR 3.

Human erythrocytes infected with merozoites which had been synchronized by the Lambros-Vanderberg method (infection ratio, 0.5%; hematocrit value, 1%) and CRDS in a varying concentration were added to a 96 well microplate and cultured at 37° C. for 78 hours in the usual way, using a medium which had been prepared by dissolving 10.4 g of RPMI 1640, 5.9 g of HEPES buffer, 4.0 g of glucose and 44 mg of hypoxanthine in 1 liter of water and adding gentamicin to the resulting solution to its concentration of 50 mg/ml. Growth of merozoites was measured based on the uptake of tritium ($^3$H)-labeled hypoxanthine to examine the effect of CRDS to inhibit the infection.

Figure 1A:
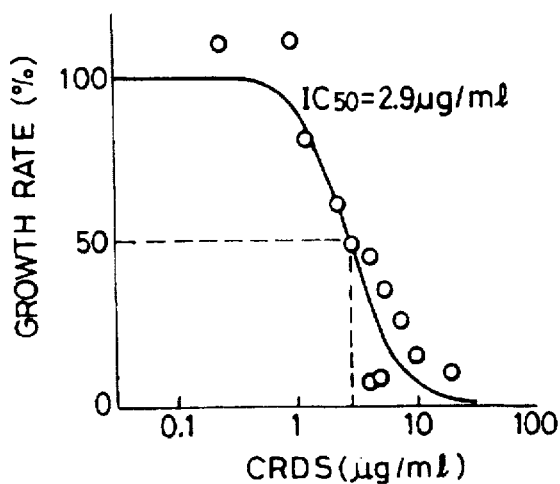
FIGS. 1 to 3 show the results of Test Examples 1 to 3, respectively.
Figure 1B:
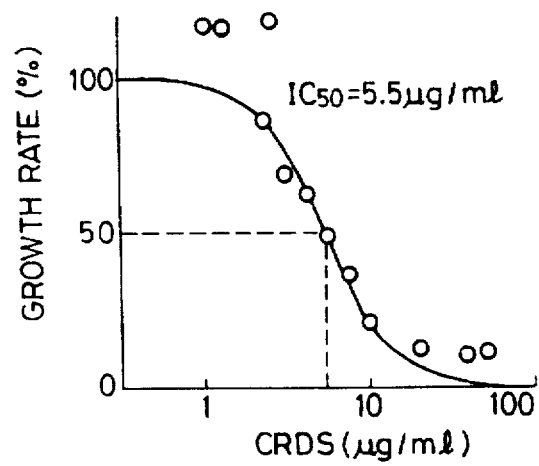
Figure 1C:
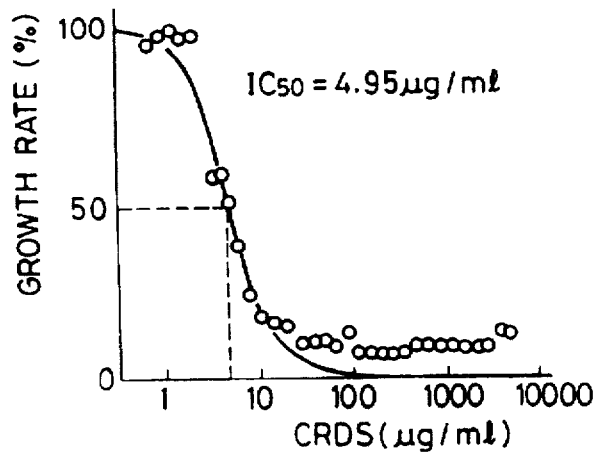

This test was carried out three times, and 50% inhibition concentration ($IC_{50}$) was determined for each run. The results are shown in FIG. 1. The $IC_{50}$ values were 2.9, 5.5 and 4.95 µg/ml, respectively.

Text Example 2

In order to examine the effect of the joint use of sulfated curdlan (CRDS) and quinine on the chloroquine-resistant *P.*

*falciparum* strain FCR 3, another test similar to Test Example 1 was carried out by changing the ratio of both ingredients to determine $IC_{50}$ at each ratio.

Human erythrocytes infected with merozoites which had been synchronized by the Lambros-Vanderberg method (infection ratio, 0.5%;, hematocrit value, 1%) and CRDS (the same material used in Test Example 1) and quinine were added at a certain CRDS to quinine ratio but to their varying concentration, to a 96 well microplate and cultured at 37° C. for 78 hours in the usual way using the medium described in Test Example 1. Growth of merozoites was measured based on the incorporation of tritium ($^3$H)-labeled hypoxanthine to examine the effect of the joint use of CRDS and quinine on the inhibition of the infection.

Figure 2:
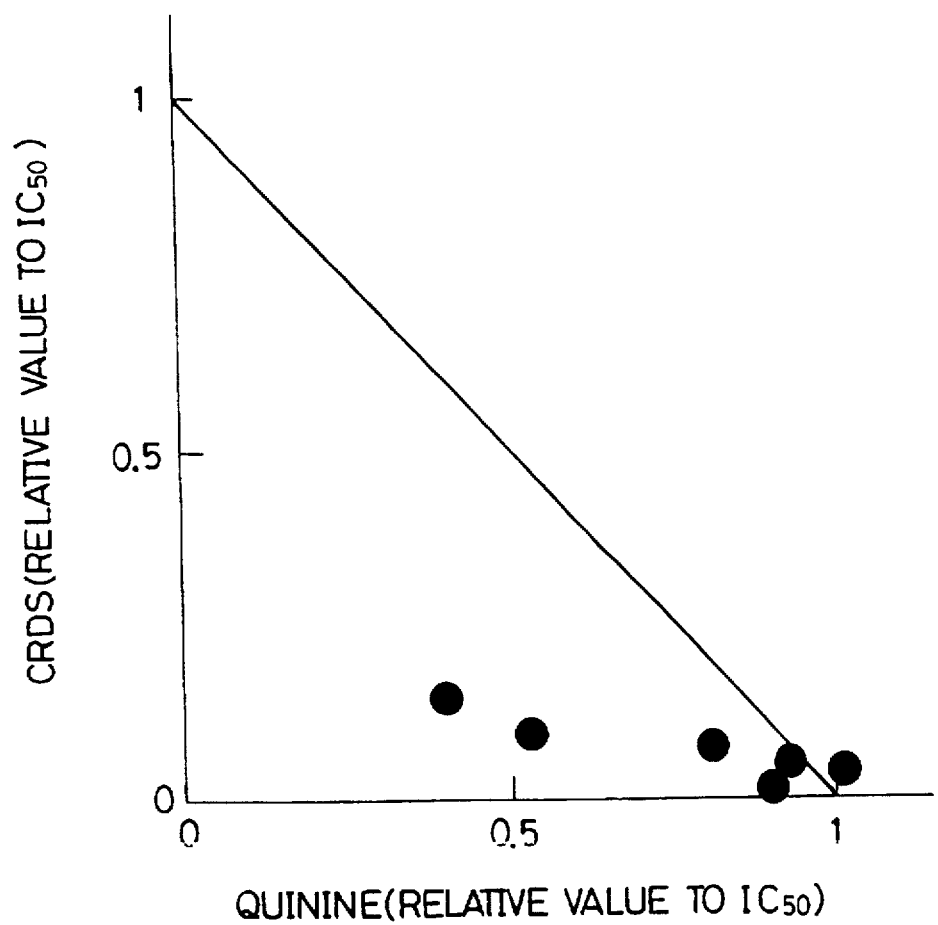

Concentrations of CRDS and quinine to inhibit 50% of the growth at each ratio were measured, and their relative values to the $IC_{50}$ of each drug when used alone (CRDS, 4.95 μg/ml; and quinine, 41.6 nM) were plotted to prepare an isobologram. The results are shown in FIG. 2. Since each plot was found under the straight line between the $IC_{50}$ values of both drugs when used alone, it was confirmed that CRDS and quinine exert a synergistic effect.

Test Example 3

Effect of sulfated curdlan (CRDS) to inhibit malarial infection was examined using a mouse model system.

A total of $10^6$ mouse erythrocytes infected with a mouse Haemosporina, *Plasmodium berghei*, were inoculated into the abdominal cavity of each BALB/C mouse (male) of about 25 g in body weight, thereby effecting infection. When the parasites grew and the parasite blood became around 10% of the total blood, CRDS (the same material used in Test Example 1) was subcutaneously administered in a dose of 0, 50, 100 or 200 mg/kg/day, with each daily dose divided into 4 doses per day for 6 hour-interval use.

Figure 3:
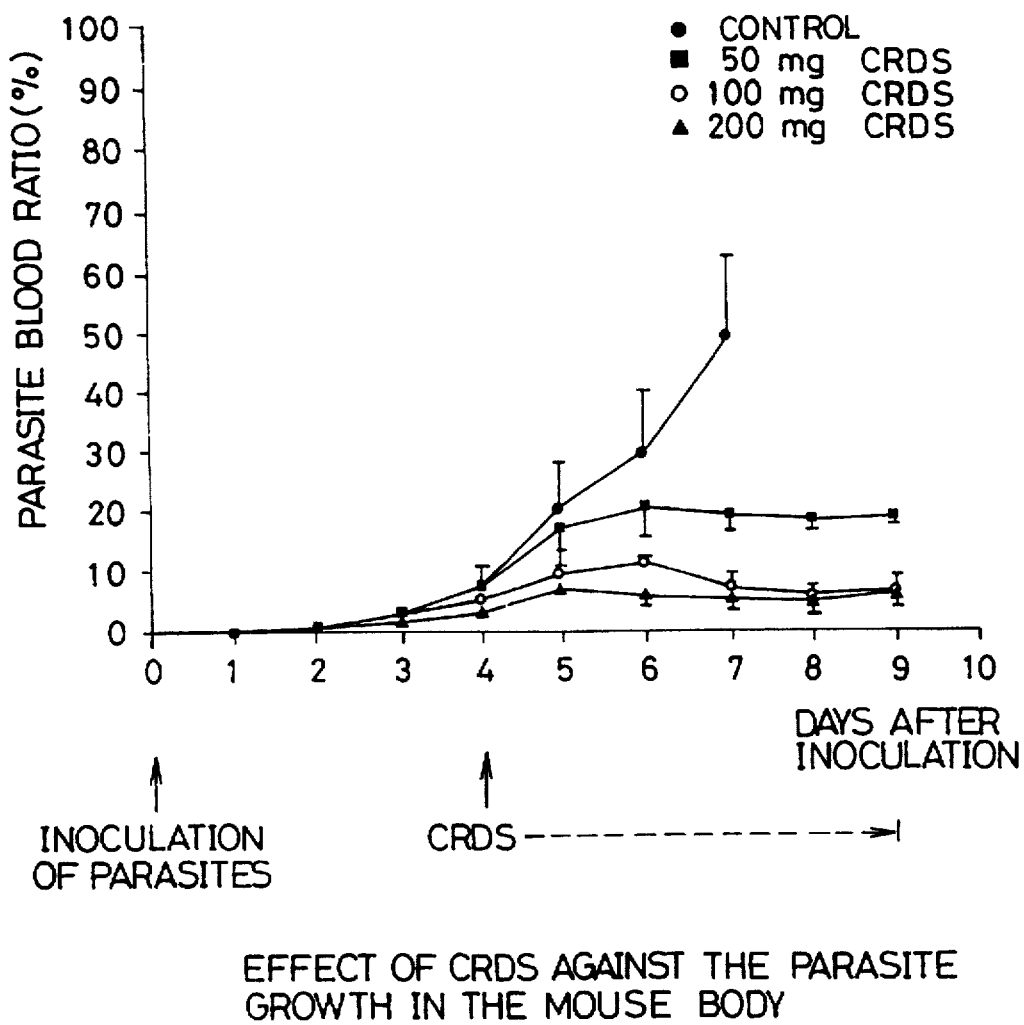

The parasite blood ratio was measured every day. The results are shown in FIG. 3. It was confirmed that the infection inhibiting effect increases as the dose of CRDS increases.

(Industrial Applicability)

The present invention has rendered possible provision of an excellent and novel antimalarial drug.

We claim:

1. A method for treating malaria in a patient, comprising administering to said patient an effective amount of a sulfated curdlan or a pharmaceutically acceptable salt thereof.

2. The method according to claim 1, wherein a synergistically effective amount of quinine is additionally administered to said patient.

* * * * *